(12) United States Patent
Nakamura et al.

(10) Patent No.: US 12,426,878 B2
(45) Date of Patent: Sep. 30, 2025

(54) MEDICAL STAPLER AND SUTURING METHOD

(71) Applicants: OLYMPUS CORPORATION, Tokyo (JP); National Cancer Center, Tokyo (JP)

(72) Inventors: Takashi Nakamura, Hachioji (JP); Satoru Nonaka, Tokyo (JP); Ichiro Oda, Tokyo (JP); Seiichiro Abe, Tokyo (JP)

(73) Assignees: National Cancer Center, Tokyo (JP); OLYMPUS CORPORATION, Tokyo (JP)

( * ) Notice: Subject to any disclaimer, the term of this patent is extended or adjusted under 35 U.S.C. 154(b) by 295 days.

(21) Appl. No.: 18/337,255

(22) Filed: Jun. 19, 2023

(65) Prior Publication Data

US 2023/0329705 A1    Oct. 19, 2023

Related U.S. Application Data

(63) Continuation of application No. PCT/JP2020/048452, filed on Dec. 24, 2020.

(51) Int. Cl.
*A61B 17/068*    (2006.01)
*A61B 17/00*    (2006.01)

(52) U.S. Cl.
CPC .. *A61B 17/068* (2013.01); *A61B 2017/00296* (2013.01); *A61B 2017/00358* (2013.01)

(58) Field of Classification Search
CPC ............... A61B 17/068; A61B 17/072; A61B 17/07207; A61B 17/1114;

(Continued)

(56) References Cited

U.S. PATENT DOCUMENTS

2004/0138682 A1* 7/2004 Onuki ............... A61B 17/0643
606/205
2018/0042603 A1 2/2018 Mitelberg et al.
(Continued)

FOREIGN PATENT DOCUMENTS

| JP | 2004041733 A | 2/2004 |
|---|---|---|
| JP | 2019526401 A | 9/2019 |
| WO | WO-2018031696 A1 | 2/2018 |

OTHER PUBLICATIONS

"International Application Serial No. PCT/JP2020/048452, International Search Report dated Feb. 9, 2021", w/ English Translation, (Feb. 9, 2021), 4 pgs.

*Primary Examiner* — Diane D Yabut
(74) *Attorney, Agent, or Firm* — Schwegman Lundberg & Woessner, P.A.

(57) ABSTRACT

A medical stapler includes an attachment-detachment portion that is attachable to and detachable from a distal-end portion of an endoscope; a grasping portion arranged at a distal-end side of the attachment-detachment portion and configured to grasp target tissue and suture the grasped target tissue; and an advancement-retraction mechanism configured to connect the grasping portion to the attachment-detachment portion such that the grasping portion is advanceable and retractable with respect to the attachment-detachment portion, wherein the advancement-retraction mechanism includes a wire sheath inserting through a penetration hole formed in the attachment-detachment portion, a distal end of the wire sheath is fixed to the grasping portion, and the grasping portion moves to the distal-end side by moving the wire sheath toward the distal-end side.

16 Claims, 16 Drawing Sheets

(58) Field of Classification Search
CPC .... A61B 2017/07214; A61B 2017/07257; A61B
2017/07271; A61B 2017/07278; A61B
2017/00818; A61B 2017/00296; A61B
1/00101

See application file for complete search history.

(56) References Cited

U.S. PATENT DOCUMENTS

| | | | |
|---|---|---|---|
| 2018/0338676 A1 | 11/2018 | Krimsky et al. | |
| 2020/0275925 A1* | 9/2020 | Smith | A61B 1/018 |
| 2021/0022733 A1* | 1/2021 | Smith | A61B 17/072 |

* cited by examiner

MEDICAL STAPLER AND SUTURING METHOD

The present application is a continuation application of PCT International Application No. PCT/JP2020/048452, filed on Dec. 24, 2020. The content of the above-identified PCT International Applications is incorporated herein by reference.

TECHNICAL FIELD

The present disclosure relates to a medical stapler and a suturing method.

BACKGROUND ART

In recent years, in a surgery to suture the gastrointestinal tract or the like, a medical stapler such as a stapler or the like is used. It is possible to facilitate the operations to suture the gastrointestinal tract or the like and significantly shorten the operation period by using the suitable medical stapler.

In an endoscopic suturing system disclosed in United States Patent Application, Publication No. 2018/0042603, a tissue retractor is advanceable with respect to a suturing device, and the suturing target tissues are retracted to the suturing device to be sutured by the advanced tissue retractor.

SUMMARY

According to an aspect of the present disclosure, a medical stapler includes an attachment-detachment portion that is attachable to and detachable from a distal-end portion of an endoscope; a grasping portion arranged at a distal-end side of the attachment-detachment portion and configured to grasp target tissue and suture the grasped target tissue; and an advancement-retraction mechanism configured to connect the grasping portion to the attachment-detachment portion such that the grasping portion is advanceable and retractable with respect to the attachment-detachment portion, wherein the advancement-retraction mechanism includes a wire sheath inserting through a penetration hole formed in the attachment-detachment portion, a distal end of the wire sheath is fixed to the grasping portion, and the grasping portion moves to the distal-end side by moving the wire sheath toward the distal-end side.

According to another aspect of the present disclosure, a suturing method includes a attaching step of attaching a medical stapler including a first jaw formed with a staple extraction portion and a second jaw formed with a staple reception portion to a distal-end portion of an endoscope; an insertion step of inserting the medical stapler and the endoscope into a body; a protruding step of protruding a treatment device from the distal-end portion of the endoscope; a grasping step of passing the protruded treatment device through a penetration space provided in the second jaw to grasp a target tissue; a retracting step of relatively retracting the first jaw and the second jaw with respect to the treatment device to retract the target tissue to pass through the penetration space; and a suturing step of closing the first jaw and the second jaw to suture the target tissue by the staple extraction portion and the staple reception portion that are opposite to each other.

DESCRIPTION OF EMBODIMENTS

First Embodiment

A first embodiment of the present disclosure will be described referring from FIG. 1 to FIG. 23.

Figure 1:
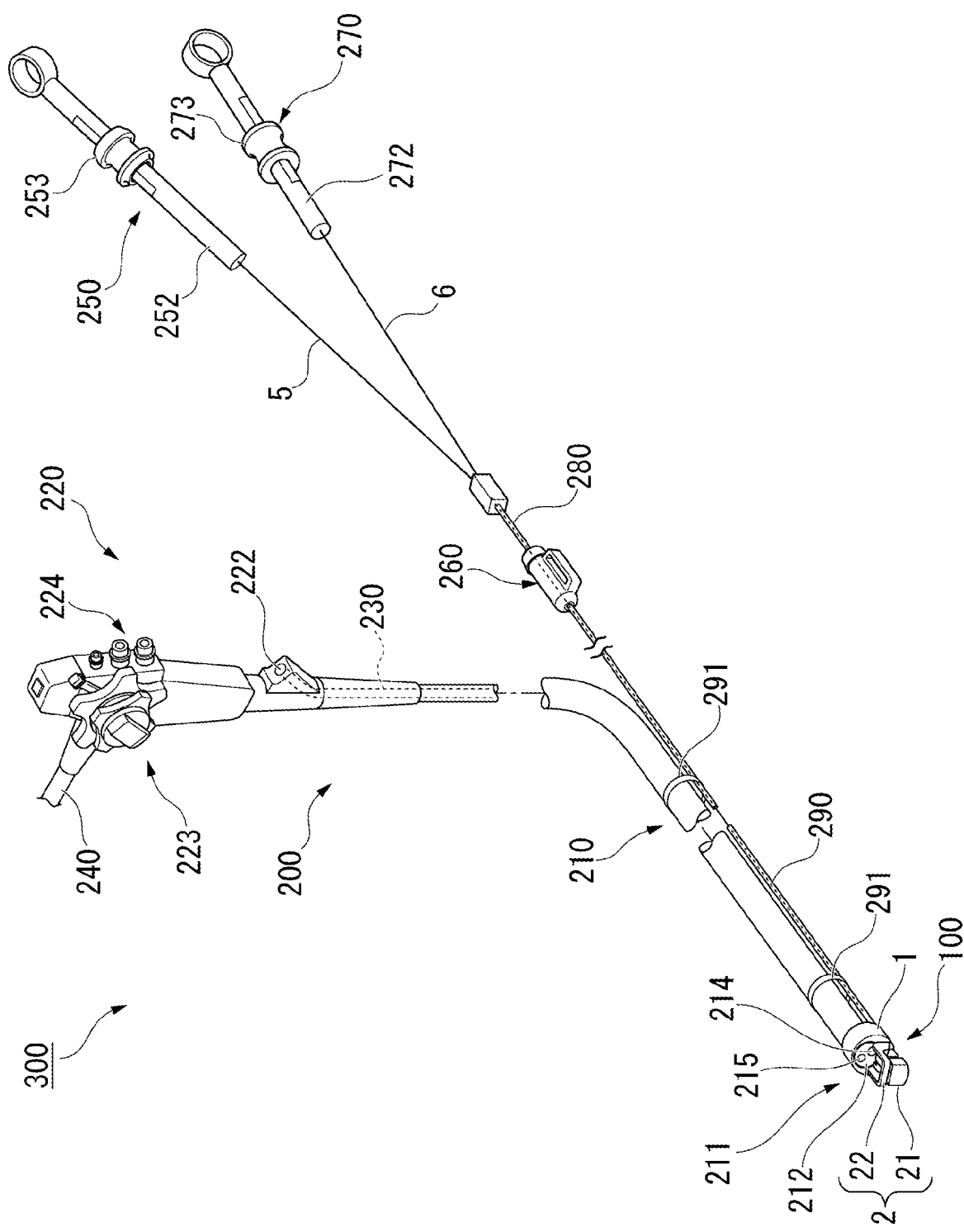
FIG. 1 is a view showing a medical system including a medical stapler according to a first embodiment of the present disclosure.

FIG. 1 is a view showing an overall configuration of a medical system 300 including a medical stapler 100 according to the present embodiment.

[Medical System 300]

The medical system 300 is used in the surgery for suturing the gastrointestinal tract or the like. The medical system 300 includes the medical stapler 100, an endoscope 200, an open-close operation portion 250, an extraction operation portion 270, a wire sheath 280, a resin sheath 290, and a wire-sheath operation portion 260.

The open-close operation portion 250 is an operation portion for operating the medical stapler 100 by an open-close operation wire (first wire) 5. The extraction operation portion 270 is an operation portion for operating the medical stapler 100 by an extraction operation wire (second wire) 6.

[Endoscope 200]

The endoscope 200 is a conventional flexible endoscope, and the endoscope 200 includes an elongated insertion portion 210 that is inserted into the body from a distal end thereof, an operation portion 220 provided at the proximal-end portion of the insertion portion 210, and a universal cord 240.

The insertion portion 210 is formed with a treatment device channel 230 through which the endoscopic treatment device is inserted. At a distal end 212 of the insertion portion 210, a forceps port 214 as a distal-end opening of the treatment device channel 230 is provided. The treatment device channel 230 extends from the distal end 212 of the insertion portion 210 to the operation portion 220.

The distal-end portion 211 of the insertion portion 210 includes an imaging unit (not shown) including an imaging element such as a CCD or the like. An objective lens 215 of the imaging unit is exposed from the distal end 212 of the insertion portion 210. The distal-end portion 211 of the insertion portion 210 includes a rigid portion 211a at the distal-end side thereof.

At the proximal-end side of the operation portion 220, a knob 223 for operating the insertion portion 210 and a switch 224 for operating the imaging unit or the like are provided. The surgeon can bend the insertion portion 210 to a desired direction by operating the knob 220.

At the distal-end side of the operation portion 220, a forceps insertion port 222 communicating with the treatment device 230 is provided. The surgeon can insert the endoscopic treatment device into the treatment device channel 230 from the forceps insertion port 222.

The universal cord 240 connects the operation portion 220 and external peripheral devices. For example, the universal cord 240 outputs the images captured by the imaging unit to the external devices. The image captured by the imaging unit is displayed on a display device such as an LCD display or the like.

[Open-Close Operation Portion 250]

The open-close operation portion 250 is an operation portion to open and close the medical stapler 100 by operating the open-close operation wire 5. As shown in FIG. 1, the open-close operation portion 250 includes an open-close operation portion main body 252 and an open-close operation slider 253. A proximal end of the open-close operation wire 5 is connected with the open-close operation slider 253. It is possible for the surgeon to advance and retract the open-close operation wire 5 by advancing and retracting the open-close operation slider 253 with respect to the open-close operation portion main body 252 along the longitudinal direction.

[Extraction Operation Portion 270]

The extraction operation portion 270 is an operation portion to extract the staple S from the medical stapler 100 by operating the extraction operation wire 6. As shown in FIG. 1, the extraction operation portion 270 includes an extraction operation portion main body 272 and an extraction operation slider 273. A proximal end of the extraction operation wire 6 is connected with the extraction operation slider 273. The surgeon can advance and retract the extraction operation wire 6 along the longitudinal direction by advancing and retracting the extraction operation slider 273 with respect to the extraction operation portion main body 272 along the longitudinal direction.

[Wire Sheath 280]

The wire sheath 280 is a sheath through which the open-close operation wire 5 and the extraction operation wire 6 are inserted. The wire sheath 280 is a coil sheath made of a metal. The wire sheath 280 is not limited to the coil sheath made of the metal and may be a sheath in other aspects.

Two inner sheaths 282 (see FIG. 14) are inserted through the wire sheath 280. The open-close operation wire 5 and the extraction operation wire 6 are inserted into the two inner sheaths 282 respectively. The two inner sheaths 282 may be a multi-lumen tube having two lumens formed therein.

[Resin Sheath 290]

The resin sheath 290 is a sheath through which the wire sheath 280 is insertable to be advanceable and retractable therein. The resin sheath 290 is formed of a resin material. As shown in FIG. 1, the distal-end side of the resin sheath 290 is connected to the insertion portion 210 of the endoscope 200 by a band 291. In the resin sheath 290, the distal end thereof is fixed to the cap 1 of the medical stapler 100, and the proximal end thereof is fixed to the wire-sheath operation portion 260.

[Wire-Sheath Operation Portion 260]

Figure 2:
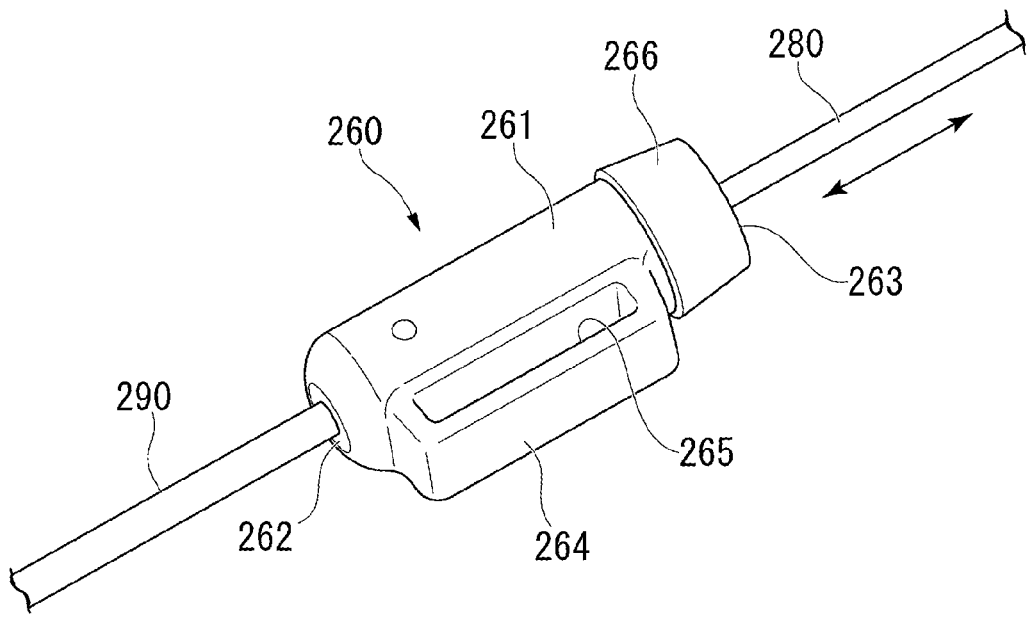
FIG. 2 is a perspective view showing a wire-sheath operation portion of the medical system.

FIG. 2 is a perspective view showing the wire-sheath operation portion 260.

The wire-sheath operation portion 260 is the operation portion for advancing and retracting the wire sheath 280 with respect to the resin sheath 290. The wire-sheath operation portion 260 includes an operation portion main body 261 and a band attachment portion 264.

The operation portion main body 261 is formed in a cylindrical shape, and the operation portion main body 261 includes a distal-end opening 262 and a proximal-end opening 263. The proximal end of the resin sheath 290 is fixed to the distal-end opening 262. The wire sheath 280 extends from the proximal-end opening 263. The surgeon can advance and retract the wire sheath 280 with respect to the resin sheath 290 by advancing and retracting the wire sheath 280 with respect to the operation portion main body 261.

The band attachment portion 264 is a member attached to the operation portion main body 261, and the band attachment portion 264 includes a band insertion hole 265. The band that is not shown in figures and passing through the band insertion hole 265 is attached to the endoscope 200 so as to simply fix the operation portion main body 261 to the endoscope 200. By fixing the operation portion main body 261 to the endoscope 200, it is possible for the surgeon to advance and retract the wire sheath 280 with respect to the resin sheath 290 without holding the operation portion main body 261 in hands.

A rubber stopper 266 in contact with the wire sheath 280 is provided at the proximal-end opening 263 from which the wire sheath 280 extends outside. Due to the friction force generated between the wire sheath 280 and the rubber stopper 266, it is possible to prevent any unintentionally advancement and retraction of the wire sheath 280 during the treatment.

[Medical Stapler 100]

Figure 3:
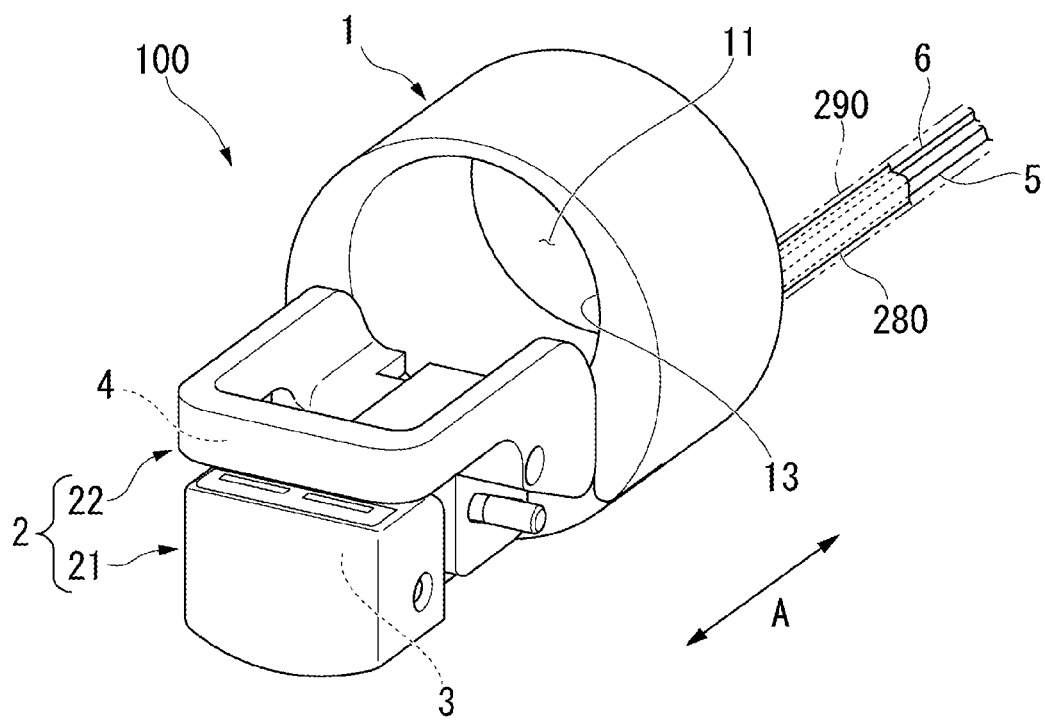
FIG. 3 is a perspective view showing the medical stapler.

FIG. 3 is a perspective view showing the medical stapler 100 according to the present embodiment.

The medical stapler 100 includes a cap 1, a grasping portion 2, a staple extraction portion 3, a staple reception portion 4, the open-close operation wire 5, and the extraction operation wire 6. The medical stapler 100 is attachable to and detachable from the distal end portion 211 of the insertion portion 210.

Figure 4:
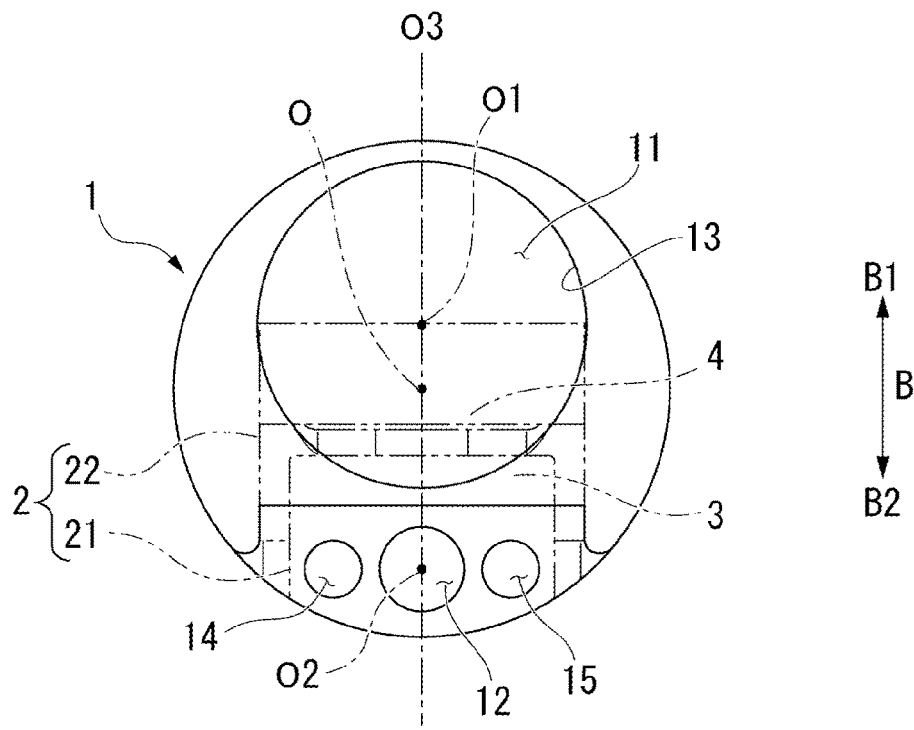
FIG. 4 is a front view showing a cap of the medical stapler.

FIG. 4 is a front view of the cap 1. In FIG. 4, the grasping portion 2 is transparently displayed.

The cap (attachment-detachment portion) 1 is a member that is attachable to and detachable from the distal-end portion 211 of the endoscope 200. The cap 1 is formed in an approximately cylindrical shape, and the cap 1 has a first penetration hole 11 penetrating in the axial direction A, a second penetration hole 12 penetrating in the axial direction A, a third penetration hole 14 penetrating in the axial direction A, and a fourth penetration hole 15 penetrating in the axial direction A.

The first penetration hole 11 is a hole in which the distal-end portion 211 of the insertion portion 210 is inserted. The shape of the first penetration hole 11 is formed following the exterior shape of the distal-end portion 211 of the insertion portion 210. Accordingly, the distal-end portion 211 of the endoscope 200 is inserted into the first penetration hole 11 such that the cap 1 can be attached to the distal-end portion 211 of the endoscope 200.

The central axis O1 of the first penetration hole 11 in the axial direction A is eccentrical with respect to the central axis O of the cap 1 in the axial direction A, as shown in FIG. 4. The side in which the central axis O1 is eccentrical with respect to the central axis O is defined as an "upper side B1".

The second penetration hole 12 is a hole for the resin sheath 290 to be inserted therein. An inner diameter of the second penetration hole 12 is approximately the same with the outer diameter of the resin sheath 290. The distal-end portion of the resin sheath 290 is inserted through the second penetration hole 12 to be fixed. The wire sheath 280, the open-close operation wire 5, and the extraction operation wire 6 inserting through the resin sheath 290 are inserted through the second penetration hole 12 to extend to the distal-end side.

As shown in FIG. 4, the central axis O2 of the second penetration hole 12 in the axial direction A is eccentrical with respect to the central axis O of the cap 1 in the axial direction A. The direction in which the central axis O2 is eccentrical with respect to the central axis O is opposite to the side (upper side B1) in which the central axis O1 is eccentrical with respect to the central axis O. The side in which the central axis O2 is eccentrical with respect to the central axis O is defined as a "lower side B2". In the present embodiment, the upper side B1 and the lower side B2 are sides along the up-down direction B.

The third penetration hole 14 and the fourth penetration hole 15 are formed at two sides of the second penetration hole 12 to sandwich the second penetration hole 12 therebetween in the front view viewed along the axial direction A.

Figure 5:
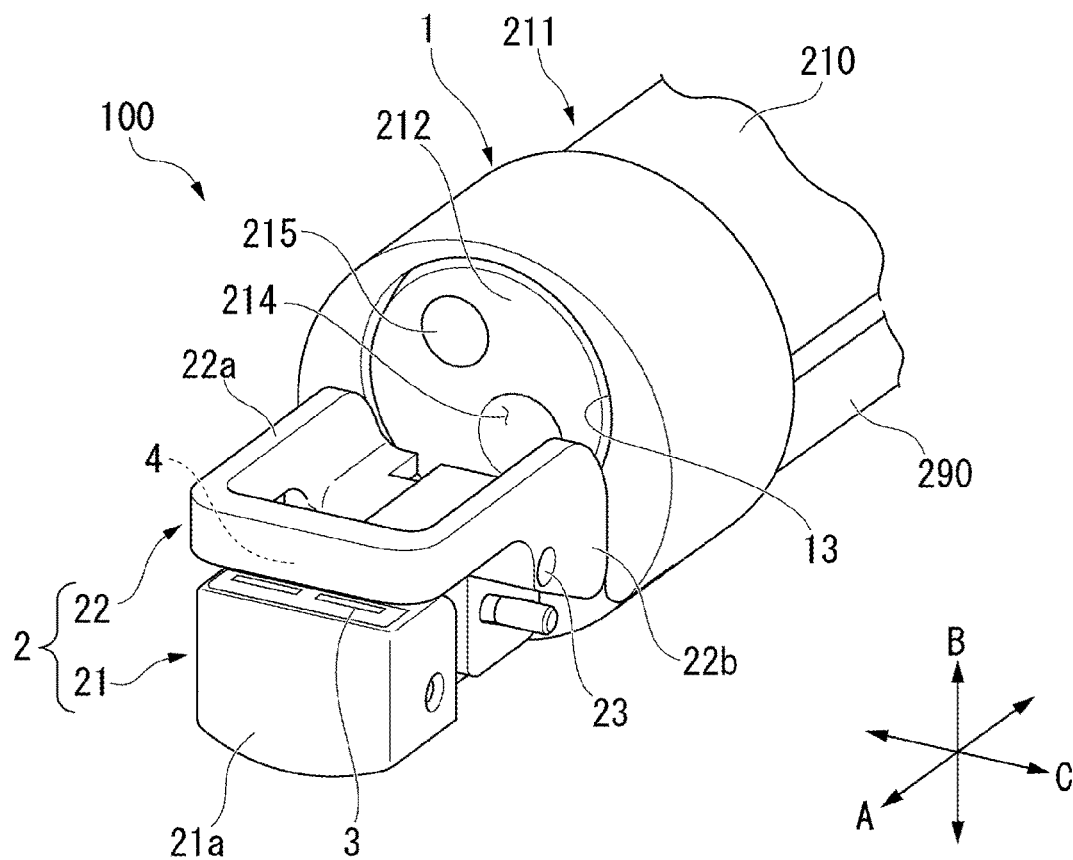
FIG. 5 is a perspective view showing the medical stapler in which a grasping portion is in a closed state.
Figure 6:
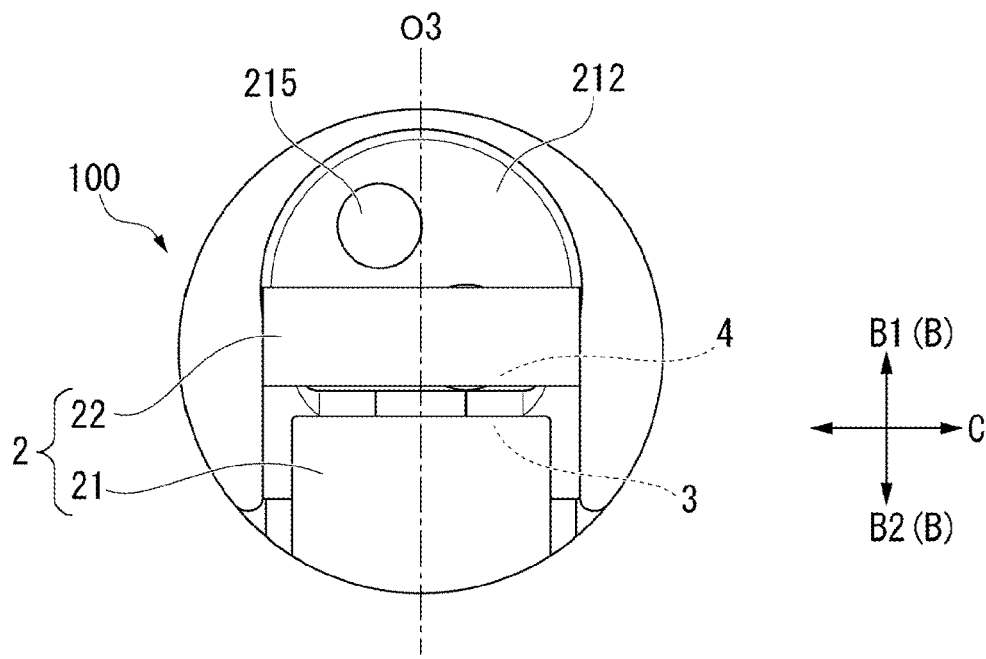
FIG. 6 is a front view showing the medical stapler in which the grasping portion is in the closed state.

FIG. 5 and FIG. 6 are a perspective view and a front view of the medical stapler 100 in which the grasping portion 2 is in the closed state, respectively.

When the cap 1 is attached to the distal-end portion 211 of the endoscope 200, as shown in FIG. 5 and FIG. 6, the objective lens 215 and the forceps port 214 are exposed from the opening 13 at the distal-end side in the first penetration hole 11 of the cap 1. The surgeon can observe the treatment target by the objective lens 215 even if the medical stapler 100 is in the state of being attached to the distal-end portion 211 of the endoscope 200.

Figure 7:
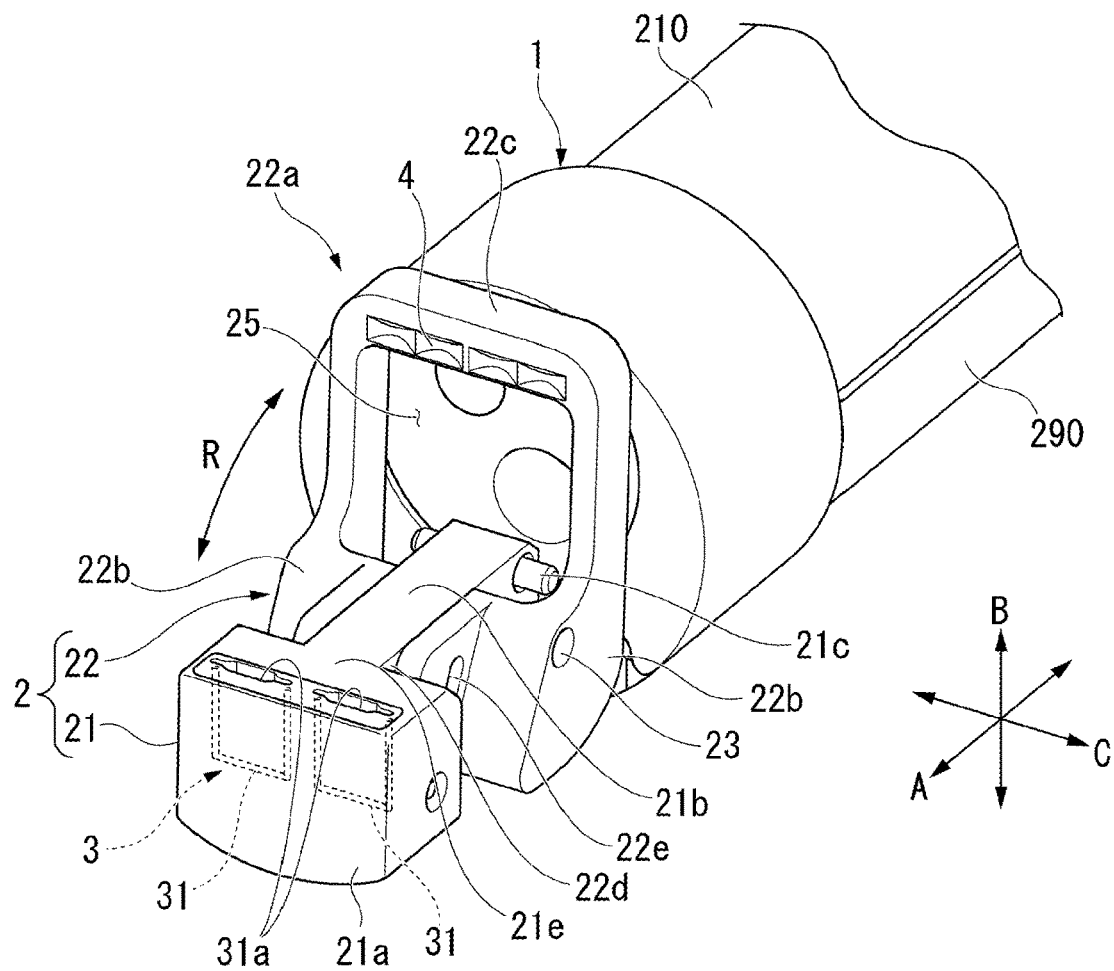
FIG. 7 is a perspective view showing the medical stapler in which the grasping portion is in an open state.
Figure 8:
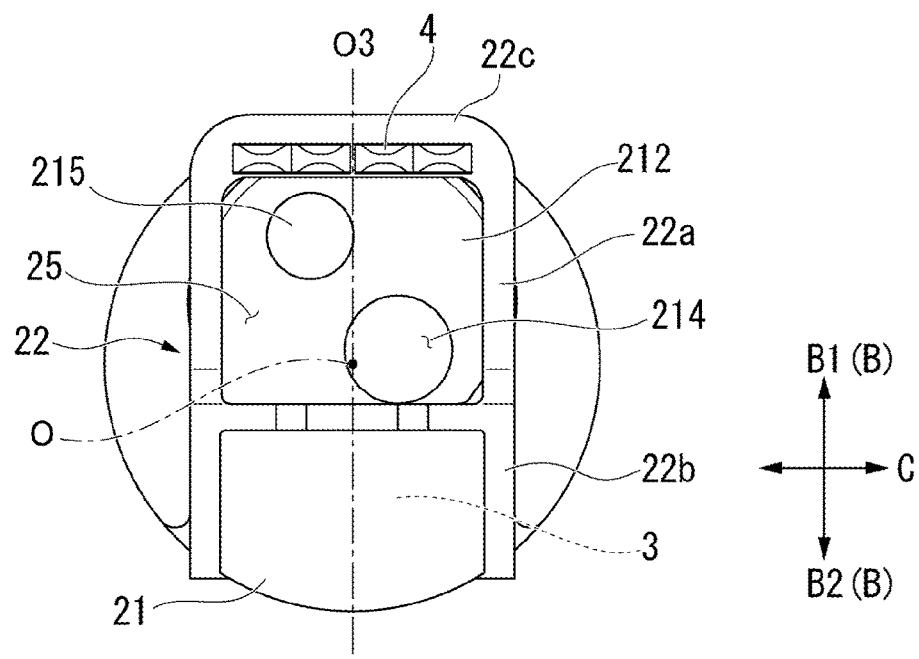
FIG. 8 is a front view showing the medical stapler in which the grasping portion is in the open state.
Figure 9:
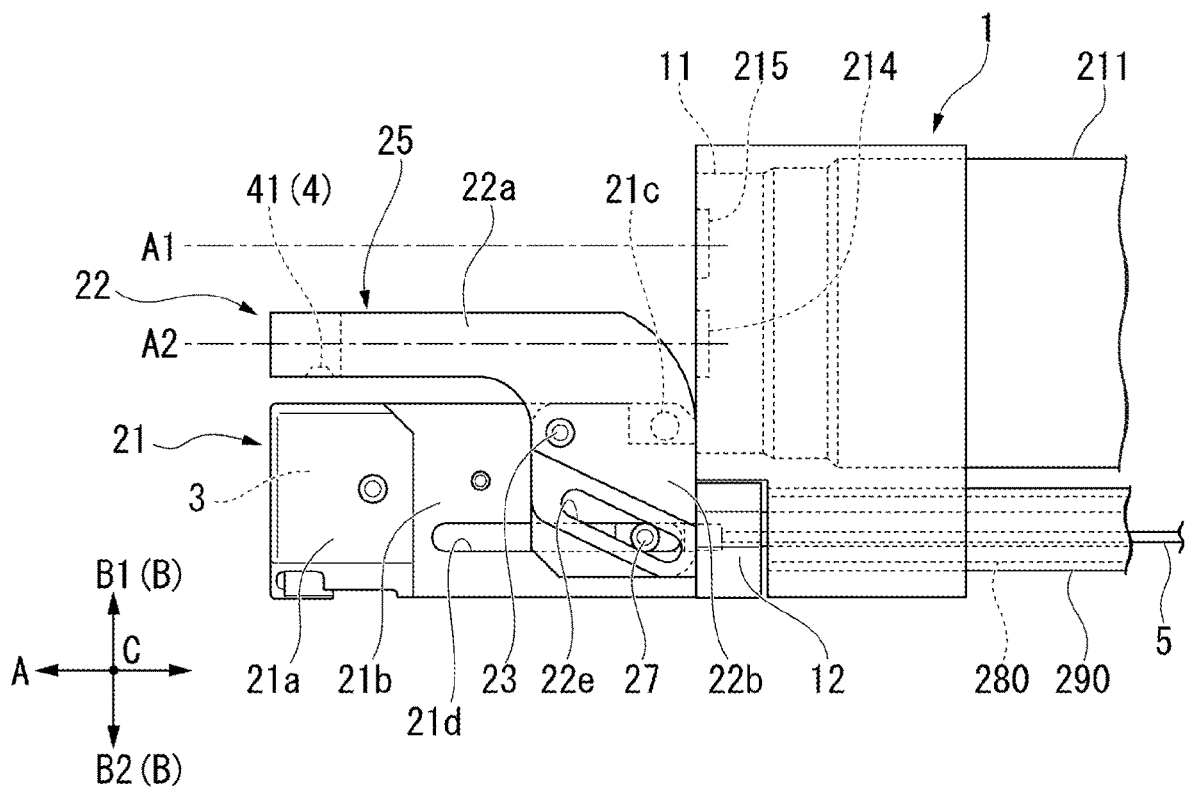
FIG. 9 is a side view showing the medical stapler in which the grasping portion is in the closed state.
Figure 10:
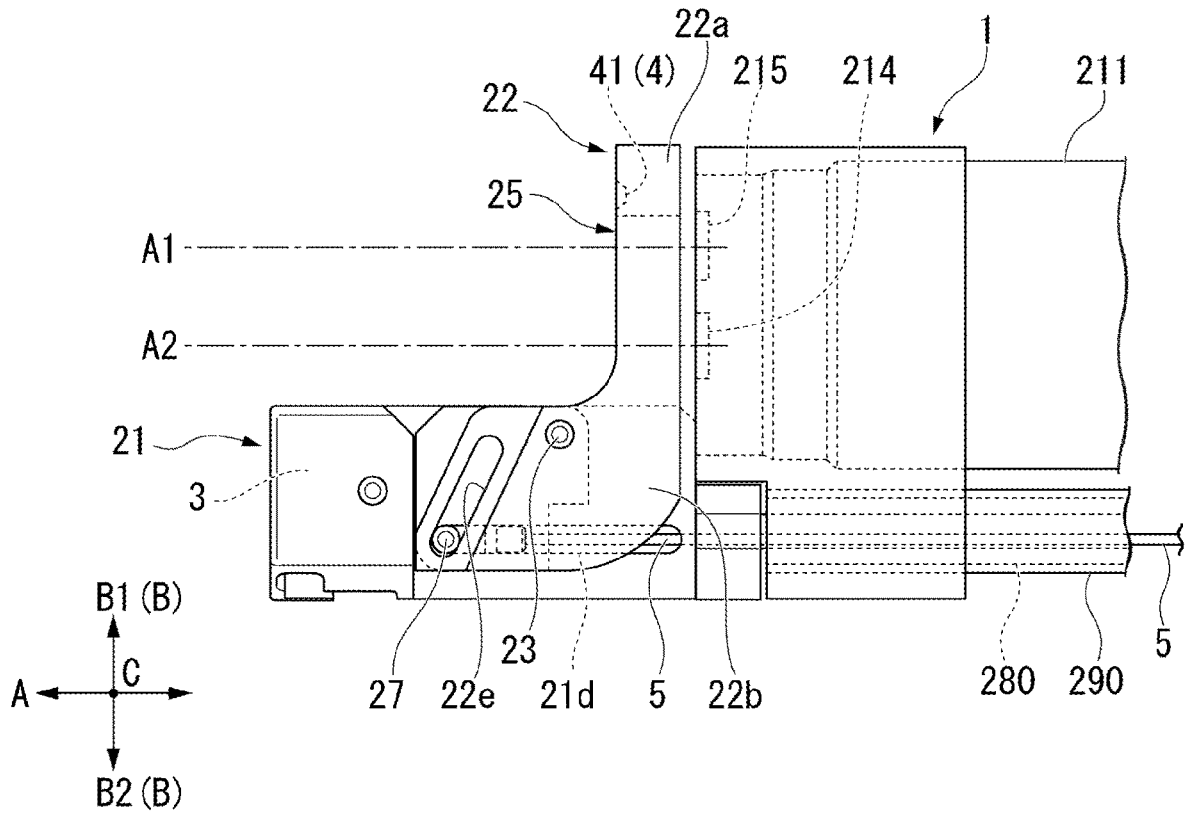
FIG. 10 is a side view showing the medical stapler in which the grasping portion is in the open state.

FIG. 7 and FIG. 8 are a perspective view and a front view of the medical stapler 100 in which the grasping portion 2 is in the open state. Furthermore, FIG. 9 is a side view of the medical stapler 100 in which the grasping portion 2 is in the closed state. FIG. 10 is a side view of the medical stapler 100 in which the grasping portion 2 is in the open state.

The grasping portion 2 is provided at the distal-end side of the cap 1 and the grasping portion 2 is possible to suture the grasped target tissue by the staples S. The grasping portion 2 includes a first grasping member (first jaw) 21, a second grasping member (second jaw) 22, an open-close rotation shaft 23, and a movable pin 27. The first grasping member 21 and the second grasping member 22 are connected by the open-close rotation shaft 23 to be openable and closeable. The first grasping member 21 and the second grasping member 22 relatively rotate with each other to grasp the target tissues. The open-close rotation shaft 23 is provided at the distal-end side of the cap 1. The axial direction C of the open-close rotation shaft 23 is orthogonal to the axial direction A of the cap 1 and the up-down direction B. As shown in FIG. 8, the grasping portion 2 is symmetrically formed with respect to the central axis O3 in the up-down direction B.

Figure 11:
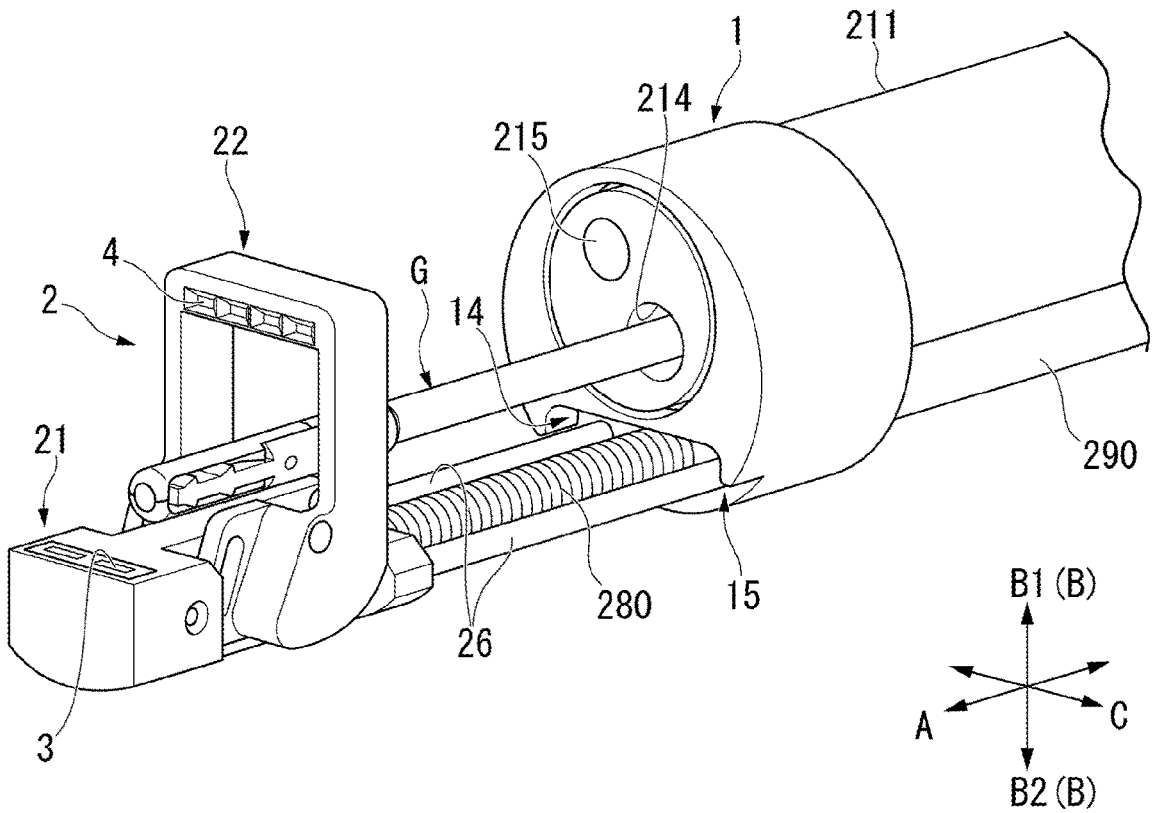
FIG. 11 is a perspective view showing a connection between a first grasping member and the cap.

FIG. 11 is a perspective view showing a connection between the first grasping member 21 and the cap 1.

The first grasping member (first jaw) 21 is connected with the distal-end side of the cap 1 to be advanceable and retractable. The first grasping member 21 is connected to the cap 1 at the lower side B2 with respect to the central axis O of the cap 1. Two support members 26 extending to the proximal-end side in the axial direction A are attached to the first grasping member 21.

The two support members 26 are rigid elongated members and configured to support the first grasping member 21 to be advanceable and retractable with respect to the cap 1. The two support members 26 are inserted through the third penetration hole 14 and the fourth penetration hole 15 respectively to be advanceable and retractable. In other words, the two support members 26, the third penetration hole 14 and the fourth penetration hole 15 configure an advancement-retraction mechanism of the first grasping member 21.

The first grasping member 21 is supported by the two support members 26 arranged to be arrayed in the width direction C so as to not to rotate around the axial direction A as the rotation center. The two support members 26 are configured to prevent the bending of the wire sheath 280 when retracting the tissues during the retraction step described below and thus have the functions of supporting the first grasping member 21 of the grasping portion 2 so as to avoid the first grasping member 21 of the grasping portion 2 from escaping from the central axis O2. If the support members 26 have enough rigidness, it is possible to provide a single support member 26.

As shown in FIG. 11, the distal-end portion of the wire sheath 280 through which the open-close operation wire 5 and the extraction operation wire 6 are inserted is fixed to the first grasping member 21. When the wire sheath 280 advances and retracts with respect to the resin sheath 290, the first grasping member 21 connected with the wire sheath 280 advances and retracts with respect to the cap 1.

As shown in FIG. 4, the first grasping member 21 is arranged at a position overlapping the second penetration hole 12 in the front view. On the other hand, as shown in FIG. 8, the first grasping member 21 is arranged at a position not to overlap the objective lens 215 and the forceps port 214 of the endoscope 200 in the front view.

As shown in FIG. 7, the first grasping member 21 includes a first distal-end portion 21a and a first main body portion 21b, and the first grasping member 21 is formed in an approximately T-shape in a planar view. The first distal-end portion 21a is arranged at the distal-end side than the first main body portion 21b.

The first distal-end portion 21a is formed in a substantially rectangular parallelepiped shape. The first distal-end portion 21a is formed in a rectangular shape extending in the axial direction C of the open-close rotation shaft 23 in the planar view. The staple extraction portion 3 is provided in the first distal-end portion 21a. The opening 31a of the staple extraction portion 3 is provided on the surface (upper surface 21e) at the upper side B1 of the first distal-end portion 21a.

The first main body portion 21b is an elongated member extending in the axial direction A. The distal end of the first main body portion 21b is fixed to the first distal-end portion 21a. The proximal end of the first main body portion 21b is fixed to the cap 1. The first main body portion 21b includes an abutting pin 21c and a first engagement groove 21d.

The abutting pin 21c is provided at the proximal end of the first main body portion 21b, and the abutting pin 21c is configured to abut to the second grasping member 22 in the closed state to regulate the movable range of the second grasping member 22.

The first engagement groove 21d shown in FIG. 9 is a groove penetrating in the axial direction C of the open-close rotation shaft 23 in the first main body portion 21b. The first engagement groove 21d extends in the axial direction A.

The second grasping member (second jaw) 22 is attached to the first grasping member 21 by the open-close rotation shaft 23 to be rotatable. The second grasping member 22 includes a U-shaped member 22a substantially formed in the U-shape and a second main body portion 22b to rotatably support the U-shaped member 22a.

The U-shaped member 22a is formed in the substantially U-shape, wherein two end portions thereof are connected with the second main body portion 22b, and the central portion thereof is disposed at the distal-end side. The central portion includes the second distal-end portion 22c. The second distal-end portion 22c is formed in a substantially rectangular parallelepiped shape. The staple reception portion 4 is provided in the second distal-end portion 22c.

The second main body portion 22b is attached to the first main body portion 21b of the first grasping member 21 by the open-close rotation shaft 23 to be rotatable. The guide groove 22d into which the first main body portion 21b is inserted is formed in the second main body portion 22b. The second engagement groove 22e is formed in two side portions of the guide groove 22d of the second main body portion 22b.

The second engagement groove 22e is the groove formed in the second main body portion 22b. The second engagement groove 22e is the groove penetrating in the axial direction C. In the side view, the second engagement groove 22e is formed at the opposite side with respect to the staple reception portion 4 to sandwich the open-close rotation shaft 23. The second engagement groove 22e is symmetrical with respect to the central axis O3 of the second grasping member 22.

As shown in FIG. 7, the second grasping member 22 includes visual-field space (penetration space) 25 between the staple reception portion 4 at the distal-end side and the open-close rotation shaft 23 at the proximal-end side and penetrating in the open-close direction R. In the present embodiment, the visual-field space 25 is the space being surrounded by the sides of the U-shaped member 22a that is substantially formed in the U-shape.

The movable pin 27 is engaged with the first engagement groove 21d and the second engagement groove 22e, and the movable pin 27 advances and retracts in the axial direction A along the first engagement groove 21d. The distal end of the open-close operation wire 5 is attached to the movable pin 27. As shown in FIG. 10, when the open-close operation wire 5 advances to the distal-end side, the movable pin 27 rotates the second grasping member 22 about the open-close rotation shaft 23 as the rotation center such that the grasping portion 2 enters the open state. As shown in FIG. 9, when the open-close operation wire 5 retracts to the proximal-end side, the movable pin 27 rotates the second grasping member 22 about the open-close rotation shaft 23 as the rotation center such that the grasping portion 2 enters the closed state. That is, the open-close operation wire 5 is the member to relatively rotate the first grasping member 21 and the second grasping member 22 to transmit the power for grasping the target tissues to the grasping portion 2.

As shown in FIG. 6, when the grasping portion 2 is in the closed state, the staple extraction portion 3 and the staple reception portion 4 are opposite to each other. When the grasping portion 2 is in the closed state, a slightly narrow gap is formed between the staple extraction portion 3 and the staple reception portion 4. As shown in FIG. 5, FIG. 6, and FIG. 9, when the grasping portion 2 is in the closed state, the optical axis A1 of the objective lens 215 passes through the outside of the first grasping member 21 and the second grasping member 22. Also, when the grasping portion 2 is in the closed state, the central axis A2 of the forceps port 214 does not overlap the first grasping member 21 in the front view; however, the central axis A2 of the forceps port 214 is at the position overlapping the second grasping member 22.

As shown in FIG. 10, when the grasping member 2 is in the open state, the staple reception portion 4 is disposed at the proximal-end side than the open-close rotation shaft 23. As shown in FIG. 7, FIG. 8, and FIG. 10, when the grasping portion 2 is in the open state, the staple extraction portion 3 and the staple reception portion 4 are arranged at two sides of the optical axis A1 of the objective lens 215 to sandwich the optical axis A1 of the objective lens 215 therebetween. When the grasping portion 2 is in the open state, the optical axis A1 of the objective lens 215 passes through the visual-field space 25. Also, when the grasping portion 2 is in the open state, the central axis A2 of the forceps port 214 passes through the visual-field space 25.

Figure 12:
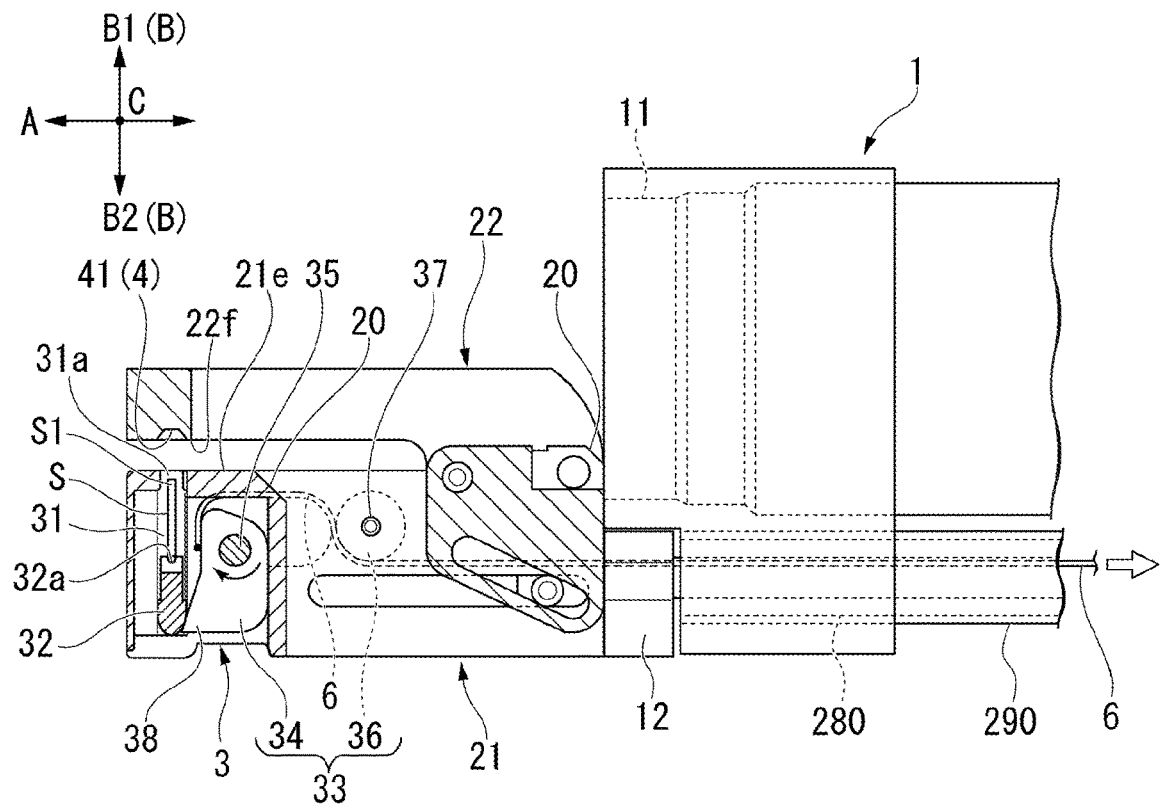
FIG. 12 is a cross-sectional view showing the grasping portion including a staple extraction portion.

FIG. 12 is a cross-sectional view showing the grasping portion 2 including the staple extraction portion 3.

The staple extraction portion 3 is arranged in the first distal-end portion 21a of the first grasping member 21 and configured to accommodate and extract the staples S. The staple extraction portion 3 includes a staple accommodation portion 31, a straight-moving member 32, and a rotation member 33.

The staple accommodation portion 31 is the space provided in the first distal-end portion 21a of the first grasping member 21 for accommodating the staples S. As shown in FIG. 7, two of the staple accommodation portions 31 are formed side by side in the axial direction C in the first grasping member 21 so as to be able to accommodate two of the U-shaped staples S.

The staple accommodation portion 31 has the opening 31a provided on the upper surface 21e of the first distal-end portion 21a to open in the up-down direction B. The staples S are accommodated in the staple accommodation portion 31 from the opening 31a. The staples S are accommodated in the staple accommodation portion 31 in the state in which the needle tip S1 of the staple S is directed toward the upper side B1.

In the planar view, the staple accommodation portion 31 is formed in a substantially rectangular shape that the short side extends in the axial direction A and the long side extends in the axial direction C. The staples S accommodated in the staple accommodation portion 31 are arranged that the needle tips S1 at two ends thereof are arrayed in the axial direction C.

The straight-moving member 32 is the member accommodated in the staple accommodation portion 31 and movable in the inside space of the staple accommodation portion 31 along the up-down direction B. The straight-moving member 32 includes a concave portion 32a at the upper side B1 to support the staple S. The staple S accommodated in the staple accommodation portion 31 is fitted into the concave portion 32a.

A first pulley 34 and a second pulley 36 as the rotation member 33 are attached to the inside of the first grasping member 21 to be rotatable, and the first pulley 34 and the second pulley 36 rotate so as to move the straight-moving member 32 in the up-down direction B. The distal-end of the extraction operation wire 6 is connected to the first pulley 34. It is possible to rotate the first pulley 34 by pulling the extraction operation wire 6.

The second pulley 36 is attached to the inside of the first grasping member 21 to be rotatable, and the first pulley 34 is disposed at the distal-end side of the second pulley 36. The rotation axis 35 of the first pulley 34 and the rotation axis 37 of the second pulley 36 extend in the axial direction C and substantially parallel to the open-close shaft 23 of the grasping portion 2. The first pulley 34 includes the convex portion (contact portion) 38 at the distal-end side to support the straight-moving member 32 from the lower side B2.

The distal end of the extraction operation wire 6 is connected to the first pulley 34 at the position at the upper side B1 than the rotation axis 35. The extraction operation wire 6 passes through the second penetration hole 12 from the first pulley 34 via the second pulley 36 to extend to the extraction operation portion 270. The reason for providing the second pulley 36 is to suitably perform the position adjustment for guiding the extraction operation wire 6 to the second penetration hole 12 and reduce the friction resistance at the time of guiding the extraction operation wire 6 to the second penetration hole 12. Accordingly, the same function can be realized by using the first pulley 34 only as the rotation member 33 and providing a member (friction-reduction member) in an R-shape and with a suitable slidability instead of the second pulley 36.

Figure 13:
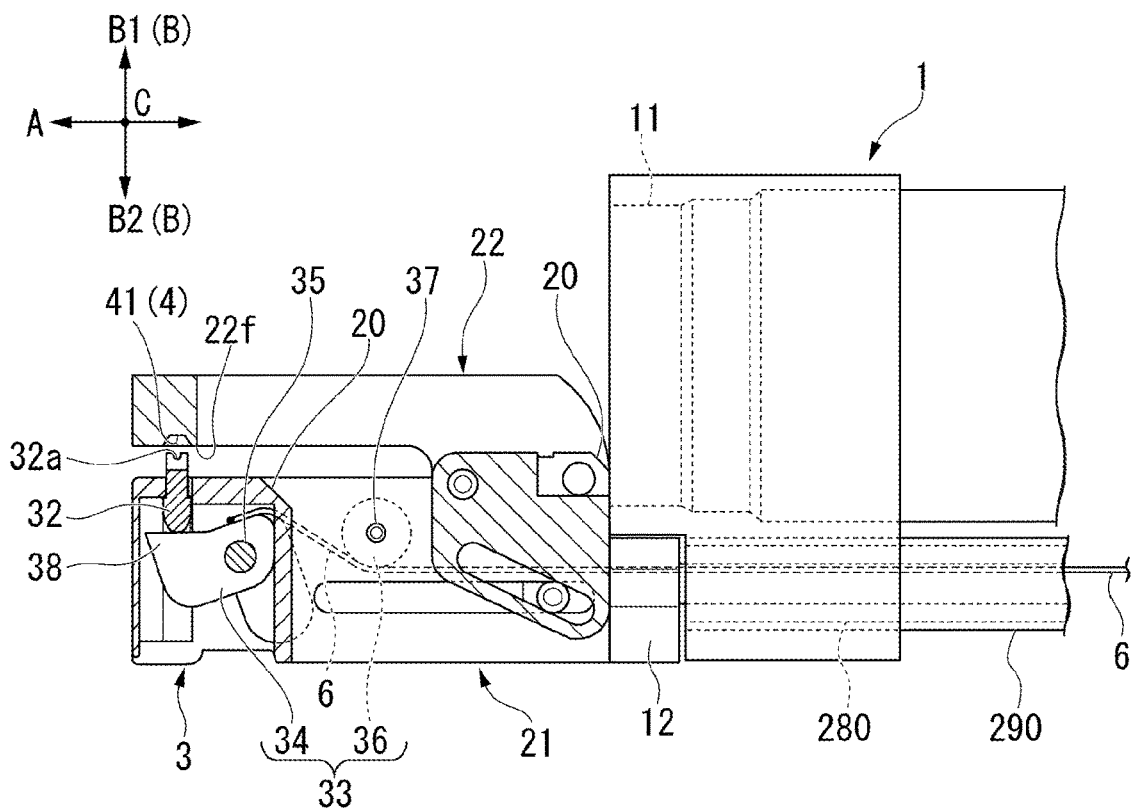
FIG. 13 is a cross-sectional view showing the grasping portion where an extraction operation wire is pulled.

FIG. 13 is a cross-sectional view showing the grasping portion 2 in which the extraction operation wire 6 is pulled.

By pulling the extraction operation wire 6, the portion at the upper-side B1 of the first pulley 34 rotates to the proximal-end side, and the portion at the lower-side B2 of the first pulley 34 rotates to the distal-end side. As a result, the convex portion 38 of the first pulley 34 pushes up the straight-moving member 32 to the upper-side B1 to extract the accommodated staple S to the upper-side b1 from the opening 31a. That is, the extraction operation wire 6 is a member to transmit the power for extracting the staple S to the grasping member 2.

The staple reception portion 4 is provided on the lower surface 22f of the second distal-end portion 22c of the second grasping member 22. The staple reception portion 4 is provided with a plurality of pockets 41 being capable of accommodating the staples extracted from the staple extraction portion 3. In the present embodiment, two of the U-shaped staples are extracted from the staple extraction portion 3 such that there are four pockets 41 being provided in the staple reception portion 4. As shown in FIG. 12, when the grasping portion 2 is in the closed state, the opening 31a from which the staple S is extracted and the pocket 41 of the staple extraction portion 3 are opposite to each other.

Figure 14:
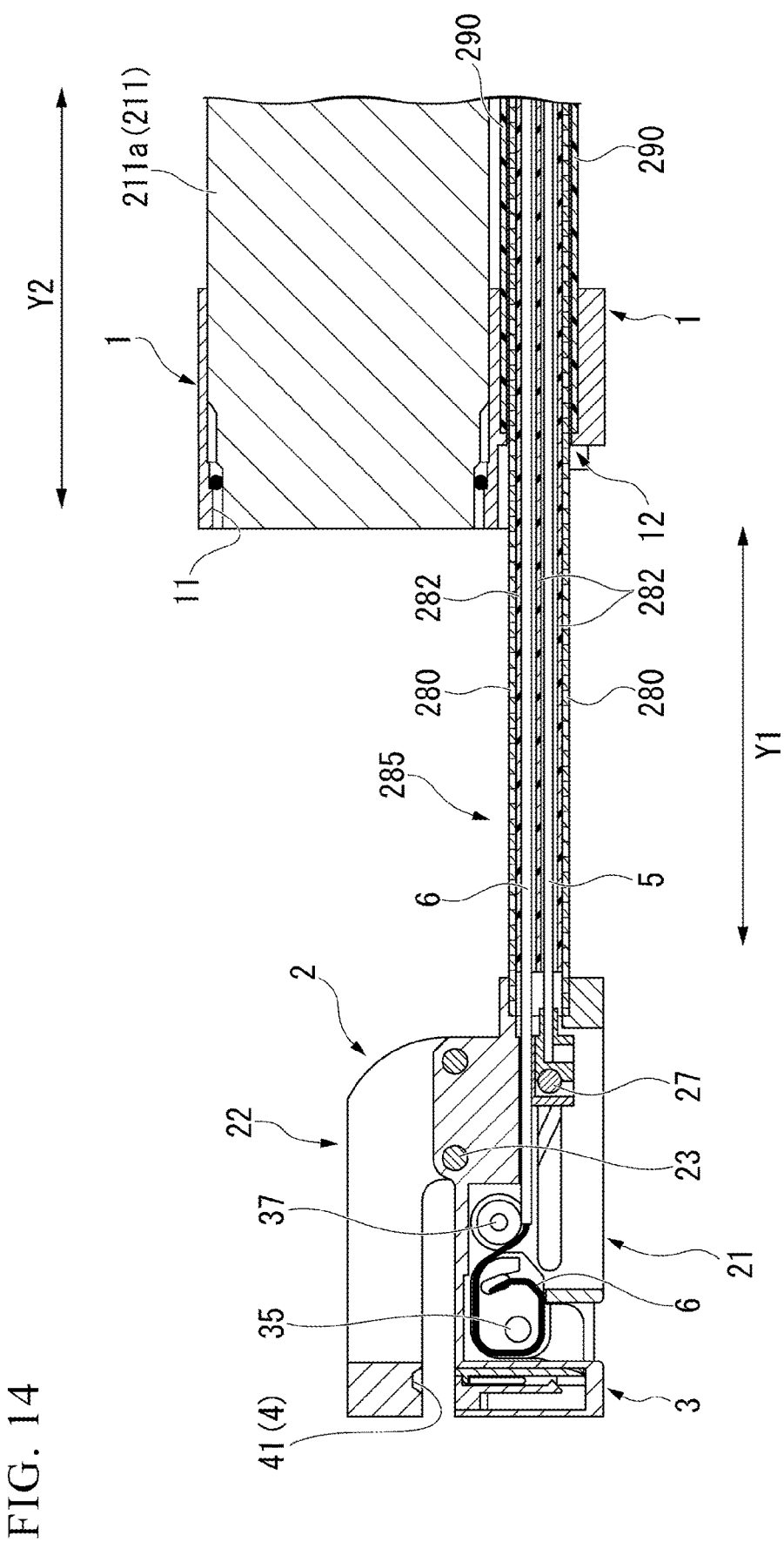
FIG. 14 is a cross-sectional view showing the advanced grasping portion and the cap.

FIG. 14 is a cross-sectional view showing the advancing grasping portion 2 and the cap 1.

Even in the advanced state, the grasping portion 2 is connected to the open-close operation wire 5 and the extraction operation wire 6 inserting through the wire sheath 280. Even in the state in which the grasping portion 2 is advanced, the surgeon can advance and retract the open-close operation wire 5 and the extraction operation wire 6.

The grasping portion 2 shown in FIG. 14 is disposed at the most-advanced position with respect to the cap 1. A length Y1 of the distal-end portion 285 being protrudable from the second penetration hole 12 of the cap 1 to the distal-end side in the wire sheath 280 is equal to or smaller than a length Y2 of the rigid portion 211a in the distal-end portion 211 of the endoscope 200.

Figure 15:
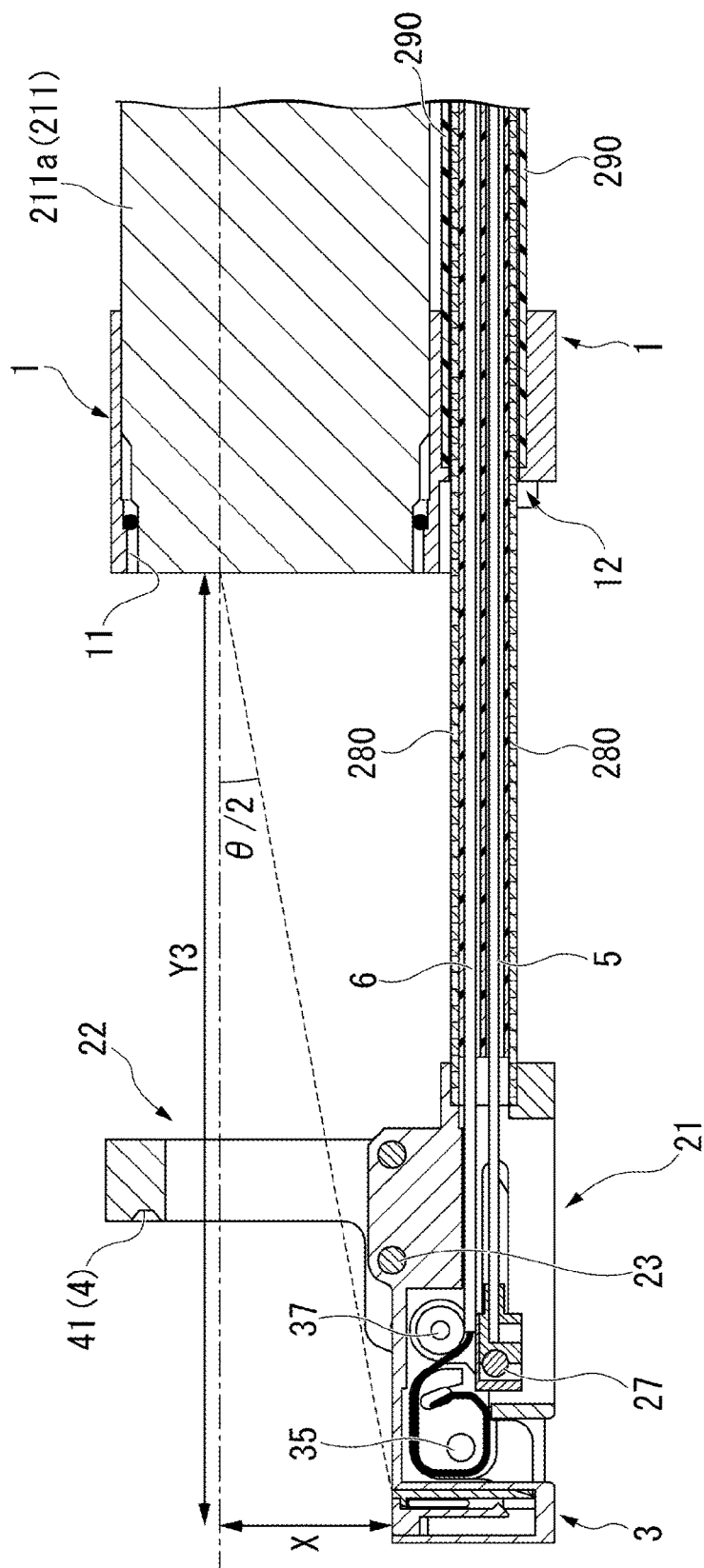
FIG. 15 is a cross-sectional view showing the advanced grasping portion in the open state and the cap.

FIG. 15 is a cross-sectional view showing the grasping portion 2 in the advanced state and the cap 1.

The grasping portion shown in FIG. 15 is disposed at the most-advanced position with respect to the cap 1. It is desirable that a length Y3 from the staple extraction portion 3 of the grasping portion 2 arranged at the most-advanced position to the objective lens 215, the distance X from the optical axis A1 of the objective lens 215 to the opening 31a of the staple extraction portion 3, and the view angle θ of the objective lens 215 satisfy the relationship according to the equation (1) shown below. In the case in which the above-described parameters satisfy the equation (1), the objective lens 215 can capture the suturing position regardless of the advancing and retracting position of the grasping portion 2.

$$X/\tan(\theta/2) \leq Y3 \quad (1)$$

[Operations of Medical Stapler 100]

Figure 16:
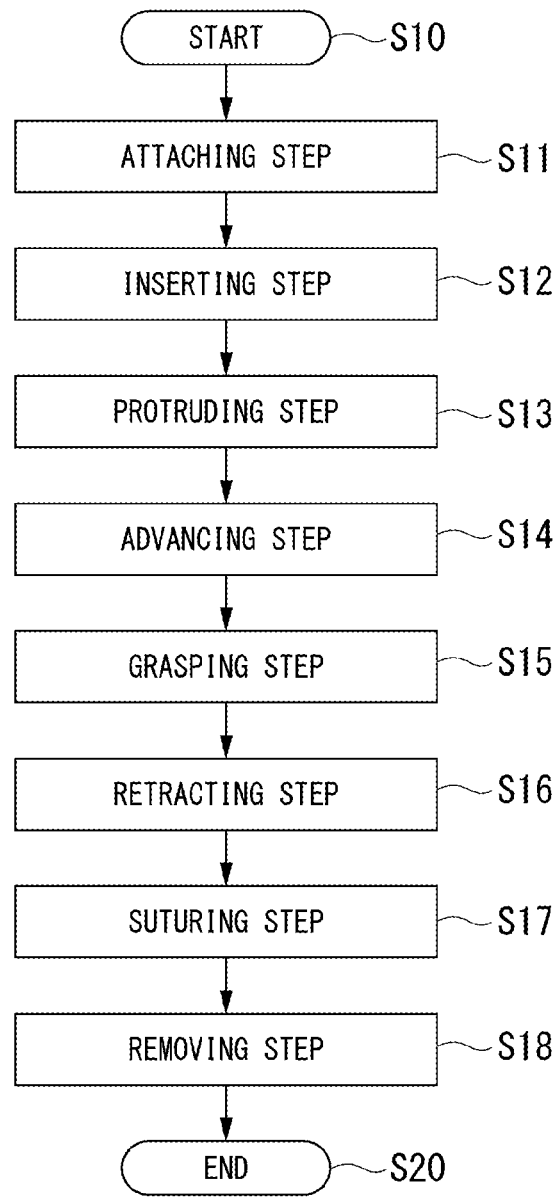
FIG. 16 is a flowchart showing the surgery procedures using the medical stapler by a surgery.

Next, the operations of the medical stapler 100 will be described. FIG. 16 is a flow chart showing the surgery procedures by the surgeon using the medical stapler 100. FIG. 17 to FIG. 23 are views for describing the operations of the medical stapler 100.

The surgeon attaches the medical stapler 100 to the distal-end portion 211 of the endoscope 200 (attaching step S11). The surgeon inserts the medical stapler 100 and the endoscope 200 into the body (inserting step S12).

Figure 17:
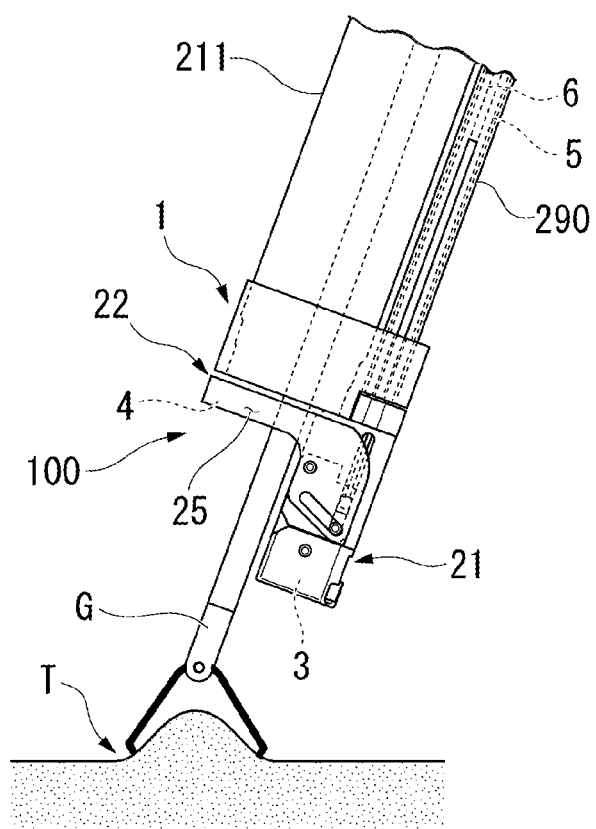
FIG. 17 is a view showing operations of the medical stapler.

The surgeon moves the distal-end portion 211 of the endoscope 200 to which the medical stapler 100 is attached to approach the treatment target T (an example of target tissues). The surgeon operates the open-close operation portion 250 to advance the open-close operation wire 5 to make the grasping portion 2 into the open state. The optical axis A1 of the objective lens 215 passes through the visual-field space 25 such that the surgeon can observe the treatment target T through the imaging unit of the endoscope 200. Also, the central axis A2 of the forceps port 214 passes through the visual-field space 25 such that as shown in FIG. 17, the surgeon can protrude the grasping forceps (treatment device) G from the forceps port 214 to perform the treatment with respect to the treatment target T (protruding step S13).

As shown in FIG. 12, in the grasping portion 2, a chamfer portion 20 is formed at the position where the protruded grasping forceps G is easy to be hooked. Accordingly, the surgeon can smoothly perform the operations of protruding the grasping forceps G.

Figure 18:
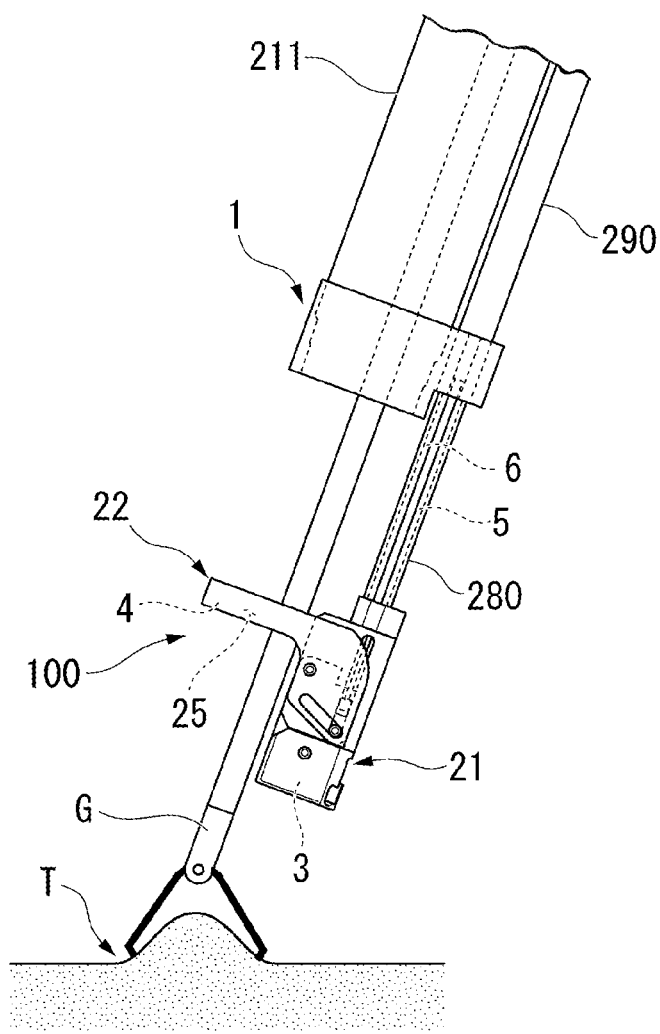
FIG. 18 is a view showing the operations of the medical stapler.

As shown in FIG. 18, in a case in which the treatment target T is at the position being difficult for the endoscope 200 to approach, the surgeon advances the grasping portion 2 by advancing the wire sheath 280 (advancing step S14). The surgeon protrudes the grasping forceps G from the visual-field space (penetration space) 25 of the advanced grasping portion 2 to grasp the treatment target T (grasping step S15).

Figure 19:
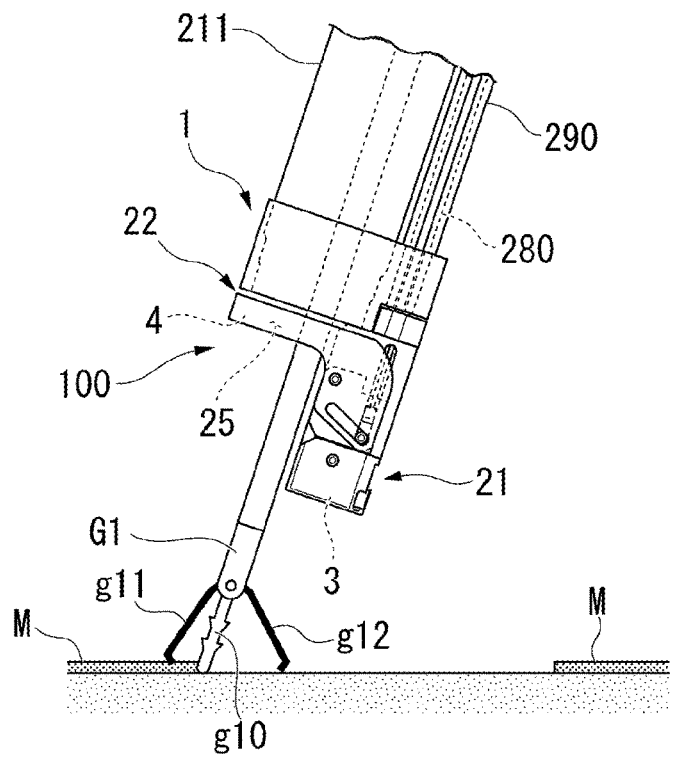
FIG. 19 is a view showing another aspect of a grasping step.
Figure 20:
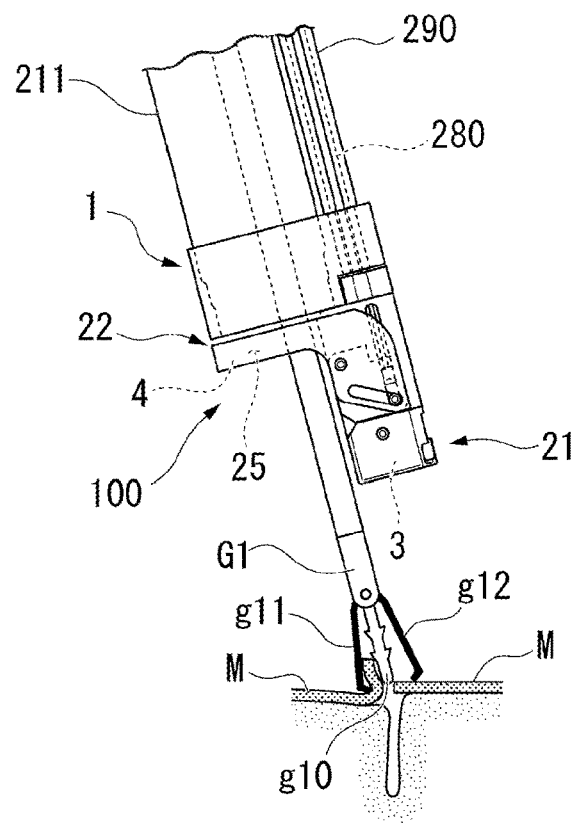
FIG. 20 is a view showing another aspect of the grasping step.

FIG. 19 and FIG. 20 are views showing other aspects of the grasping step S15.

The grasping step S15 includes the aspect of drawing the mucous membrane M at distance positions together to grasp. In this case, the grasping forceps (treatment device) including a fixed forceps piece g10, a first forceps piece g11, and a second forceps piece g12 is used. The first forceps piece g11 and the second forceps piece g12 are provided at two sides of the fixed forceps piece g10 to sandwich the fixed forceps piece g10 therebetween to be individually rotatable. As shown in FIG. 19, the surgeon grasps the mucous membrane M at one side by the fixed forceps piece g10 and the first forceps piece g1l. Then, as shown in FIG. 20, the surgeon grasps the mucous membrane M at the other side by the fixed forceps piece g10 and the second forceps piece g12.

Figure 21:
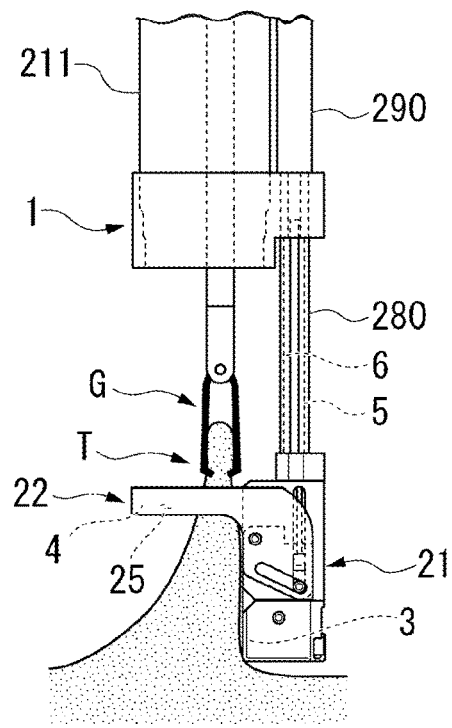
FIG. 21 is a view showing the operations of the medical stapler.

As shown in FIG. 21, the surgeon retracts the grasping forceps G in the state of grasping the treatment target T by the grasping forceps G. The surgeon retracts the grasping forceps G until the distal end of the grasping forceps G passes through the visual-field space (penetration space) 25 to retract the treatment target T until the treatment target T passes through visual-field space (penetration space) 25. As a result, the treatment target T is arranged at the proximal-end side than the stable extraction portion 3. The surgeon may advance the grasping portion 2 with respect to the grasping forceps G to retract the treatment target T. That is, the surgeon relatively retracts the grasping forceps G with respect to the grasping portion 2 to retract the treatment target T (retracting step S16).

As shown in FIG. 21, the first grasping member 21 is pressing on the peripheral portion of the treatment target T such that it is easy for the surgeon to retract the treatment target T by the grasping forceps G.

It is noted that the advancing step S14 may be performed before the grasping step S15 and before the retracting step S16. In either case, it is possible for the first grasping member 21 to press on the peripheral portion of the treatment target T in the retracing step S16.

Figure 22:
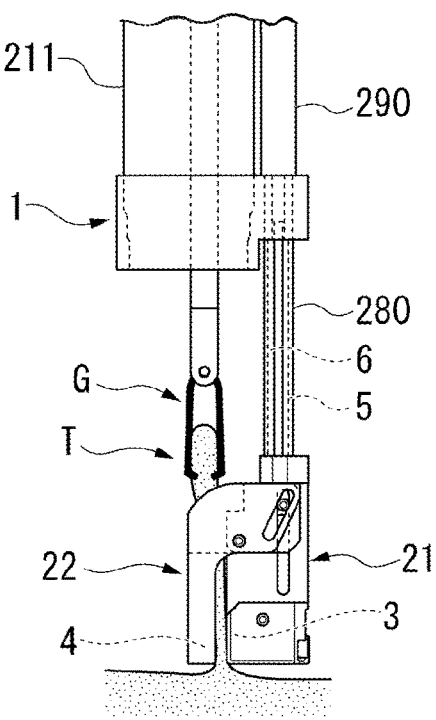
FIG. 22 is a view showing the operations of the medical stapler.

As shown in FIG. 22, the surgeon operates the open-close operation portion 250 to retract the open-close operation wire 5 to cause the grasping portion 2 in the closed state. The treatment target T is clamped by the staple extraction portion 3 of the first grasping member 21 and the staple reception portion 4 of the second grasping member 22.

When the grasping portion 2 is in the closed state, part of the treatment target T that is clamped by the grasping forceps G can be accommodated in the space (visual-field space 25) formed by the U-shaped member 22a and the second main body portion 22b of the second grasping member 22 such that it is difficult for the treatment target T that is clamped by the staple extraction portion 3 and the staple reception portion 4 to escape.

As shown in FIG. 9, when the grasping portion 2 is in the closed state, the optical axis A1 of the objective lens 215 passes through the outside of the first grasping member 21 and the second grasping member 22. Accordingly, it is also possible for the surgeon to observe the treatment target T through the imaging unit of the endoscope 200 even when the grasping portion 2 is in the closed state.

The surgeon operates the extraction operation portion 270 to pull the extraction operation wire 6 in the state in which the treatment target T is clamped by the staple extraction portion 3 and the staple reception portion 4 to extract the accommodated staples S toward the staple reception portion 4. The needle tips S1 of the staple S penetrate the treatment target T to come into contact with the pocket 41 of the staple reception portion 4 to be bent. As a result, the treatment target T is sutured (suturing step S17).

Figure 23:
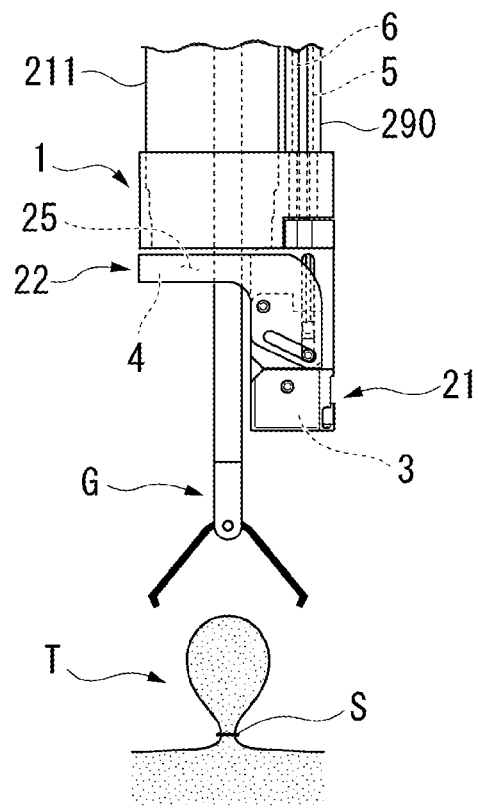
FIG. 23 is a view showing the operations of the medical stapler.

As shown in FIG. 23, the surgeon operates the open-close operation portion 250 to make the grasping portion 2 into the open state again. The surgeon separates the grasping forceps G from the treatment target T to finish the suturing treatment. The surgeon removes the medical stapler 100 and the endoscope 200 from the inside of the body (removing step S18).

In the inserting step S12 and the removing step S18, the surgeon disposes the grasping portion 2 at the most-retracted position for facilitating the passage of the medical stapler 100 through the inside of the body.

According to the medical stapler 100 disclosed in the present embodiment, the grasping portion 2 is advanceable so as to definitely suture the treatment target T at the position being difficult for the endoscope 200 to approach. The medical stapler 100 is suitable to suture the treatment target T at the position difficult for the endoscope 200 to approach.

According to the medical stapler 100 disclosed in the present embodiment, the treatment target T can be retracted with respect to the advanced grasping portion 2 by the grasping forceps G such that as shown in FIG. 22, it is possible to suture the treatment target T at a deeper position by the staple S. Accordingly, after the suturing, it is difficult for the staple S to be detached from the treatment target T.

As described above, the first embodiment of the present disclosure has been described in detail with reference to the drawings, however, the specific configuration is not limited to the present embodiment, and design changes and the like are included within the scope of the present invention. Also, the configuration elements shown in the above-described embodiment and modification examples can be combined as appropriate.

Modification Example 1

Figure 24:
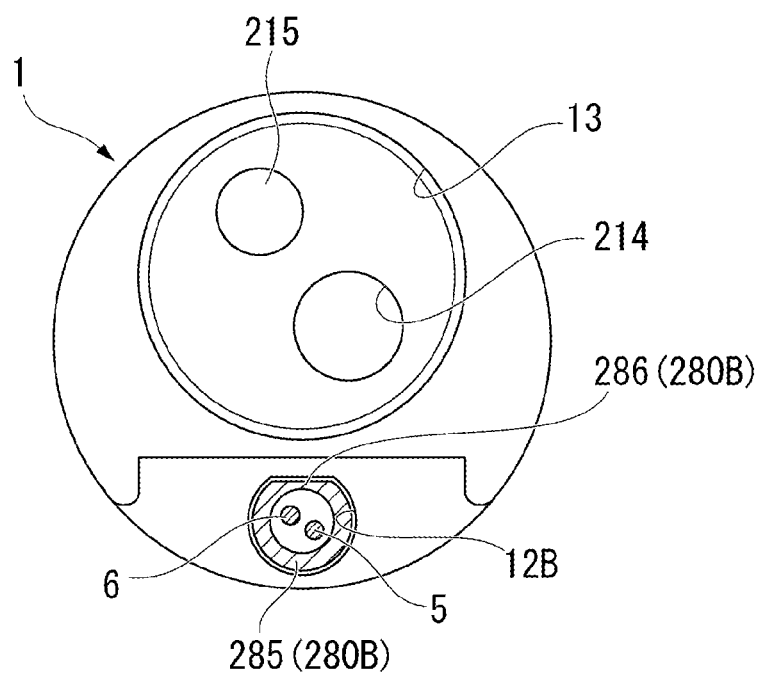
FIG. 24 is a view showing a modification example of the wire sheath.

For example, in the above-described embodiment, the first grasping member 21 is supported by the support member 26 to be advanceable and retractable. However, the aspect of the first grasping member being supported is not limited to this configuration. FIG. 24 is a view showing a wire sheath 280B as a modification example of the wire sheath 280. The distal-end portion 285 (with a length Y1) protruding from the second penetration hole 12 of the cap 1 in the wire sheath 280B is more rigid than the other portion at the proximal-end side. Accordingly, it is possible to support the advancing and retracting grasping portion 2 by the wire sheath 280B only and the support member 26 is unnecessary.

The length Y1 of the distal-end portion 285 is smaller than the length Y2 of the rigid portion 211a in the distal-end portion 211 of the endoscope 200. Accordingly, even in the case in which the grasping portion 2 retracts and the rigid distal-end portion 285 moves to the proximal-end side, the distal-end portion 285 does not move to the proximal-end side than the rigid portion 211a. Accordingly, the distal-end portion 285 does not affect the bending operations of the endoscope 200 regardless of the advancing-retracting position of the distal-end portion 285.

The distal-end portion 285 of the wire sheath 280B includes a rotation stopper 286 formed in a D shape in a cross section orthogonal to the axial direction A. A second penetration hole 12B (as a modification example of the second penetration hole 12) of the cap 1 is formed in the D shape in the cross section orthogonal to the axial direction A corresponding to the rotation stopper 286. Accordingly, the first grasping member 21 does not rotate around the axial direction A as a rotation center even without the support member 26.

Modification Example 2

Figure 25:
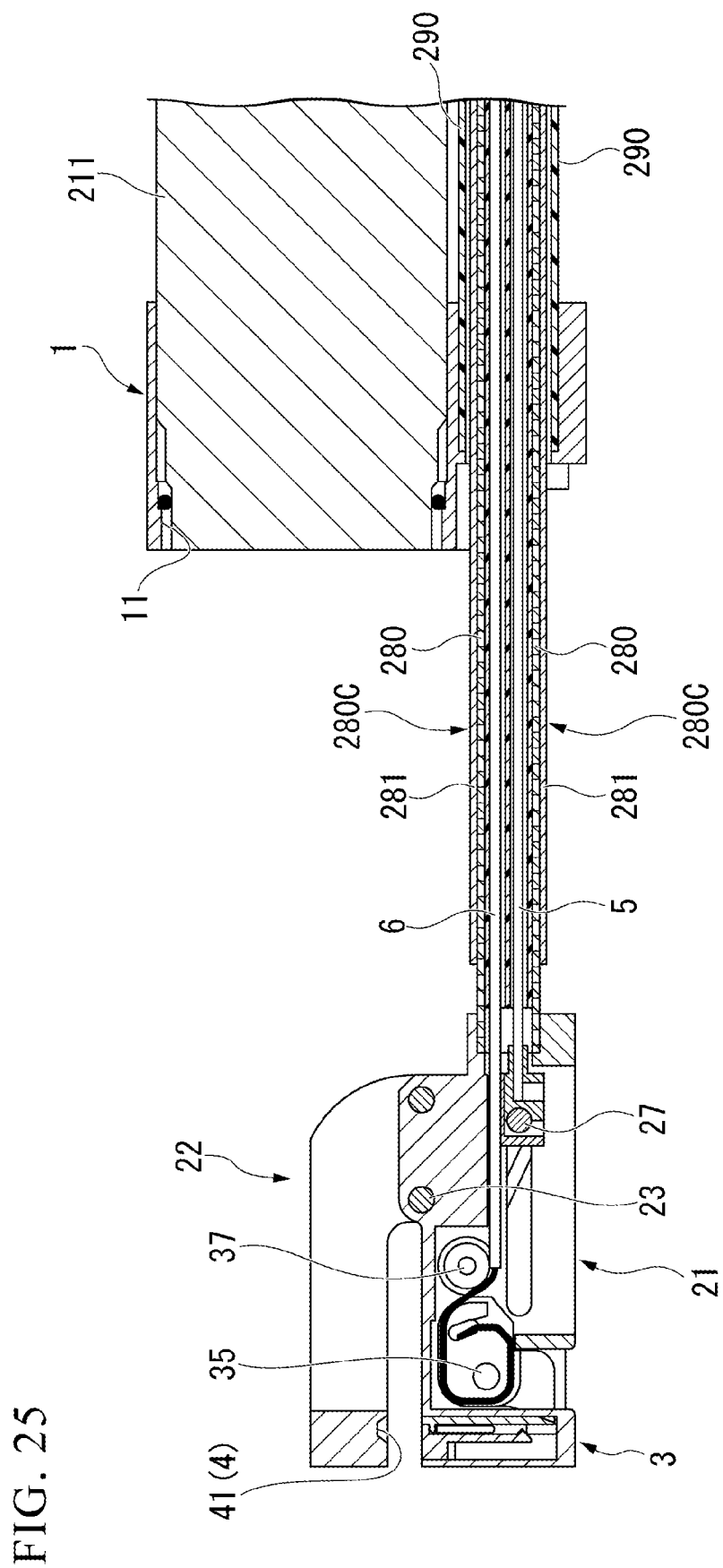
FIG. 25 is a cross-sectional view showing another modification example of the wire sheath.

FIG. 25 is a cross-sectional view showing a wire sheath 280C as another modification example of the wire sheath 280. The wire sheath 280C is a sheath configured by providing a covering layer 281 formed of the resin or the like on the outer circumference of the wire sheath 280 as the coil sheath. The wire sheath 280 is formed as the coil sheath such that there is the possibility to be extended and damaged during the advancing and retracting operations. It is possible to suitably prevent the damage of the wire sheath 280C by providing the covering layer 281.

Although the respective embodiments and modifications of the present disclosure have been described above, the technical scope of the present disclosure is not limited to the above-described embodiments, and configurations in the respective embodiments and modifications within the scope not departing from the spirit of the present disclosure. It is possible to change the combination of elements, make various changes to each configuration element, or delete each configuration element. For example, the configuration according to any one of above-described embodiments and modifications of the present disclosure may be appropriately combined with each modification of the operation section. The present disclosure is not limited by the above description, but only by the appended claims.

What is claimed is:

1. A medical stapler, comprising:
an attachment-detachment portion that is attachable to and detachable from a distal-end portion of an endoscope;
a grasping portion arranged at a distal-end side of the attachment-detachment portion and configured to grasp target tissue and suture the grasped target tissue; and
an advancement-retraction mechanism configured to connect the grasping portion to the attachment-detachment portion such that the grasping portion is advanceable and retractable with respect to the attachment-detachment portion,
wherein the advancement-retraction mechanism includes a wire sheath inserted through a penetration hole formed in the attachment-detachment portion,
a distal end of the wire sheath is fixed to the grasping portion, and
the grasping portion moves to the distal-end side by moving the wire sheath toward the distal-end side.

2. The medical stapler according to claim 1,
wherein the grasping portion includes a first jaw and a second jaw connected with each other by a rotation shaft to be openable and closable, and
the first jaw and the second jaw are configured to grasp the target tissue by relatively rotating with each other.

3. The medical stapler according to claim 2, wherein when the grasping portion is in a closed state, a staple extraction portion provided in the first jaw and a staple reception portion provided in the second jaw are opposite to each other.

4. The medical stapler according to claim 2,
wherein the attachment-detachment portion includes an opening from which a forceps port of the endoscope is exposed,
the second jaw includes a penetration space that penetrates in an open-close direction, and
when the grasping portion is in an open state, a central axis of the forceps port passes through the penetration space.

5. The medical stapler according to claim 1, further comprises:
a first wire inserted through the wire sheath and configured to transmit a power for grasping the target tissue to the grasping portion; and
a second wire inserted through the wire sheath and configured to transmit a power for extracting the staple to the grasping portion.

6. The medical stapler according to claim 1, wherein the advancement-retraction mechanism further includes a support member configured to support the grasping portion with respect to the attachment-detachment portion such that the grasping portion is advanceable and retractable.

7. The medical stapler according to claim 1, wherein a length of a distal-end portion in the wire sheath that is protrudable toward the distal-end side from the penetration hole of the attachment-detachment portion is equal to or smaller than a length of a rigid portion in the distal-end portion of the endoscope.

8. The medical stapler according to claim 7, wherein the distal-end portion of the wire sheath is more rigid than another portion at the proximal-end side of the wire sheath.

9. The medical stapler according to claim 7, wherein the distal-end portion of the wire sheath includes a rotation stopper.

10. The medical stapler according to claim 1,
wherein the attachment-detachment portion includes an opening from which an objective lens of the endoscope is exposed, and
the objective lens is configured to capture an image of the grasping portion that is advanced to the most advanced position with respect to the attachment-detachment portion.

11. The medical stapler according to claim 1, further comprises a wire-sheath operation portion configured to advance and retract the wire sheath,
wherein the wire sheath is inserted through a resin sheath whose distal end is fixed to the attachment-detachment portion, and a proximal end is fixed to the wire-sheath operation portion.

12. The medical stapler according to claim 11, wherein the wire-sheath operation portion includes a rubber stopper in contact with the wire sheath at the opening from which the wire sheath is exposed.

13. A suturing method, comprising:
an attaching step of attaching a medical stapler including a first jaw formed with a staple extraction portion and a second jaw formed with a staple reception portion to a distal-end portion of an endoscope;
an insertion step of inserting the medical stapler and the endoscope into a body;
a protruding step of protruding a treatment device from the distal-end portion of the endoscope;
a grasping step of passing the protruded treatment device through a penetration space provided in the second jaw to grasp a target tissue;
a retracting step of relatively retracting the first jaw and the second jaw with respect to the treatment device to retract the target tissue to pass through the penetration space; and
a suturing step of closing the first jaw and the second jaw to suture the target tissue by the staple extraction portion and the staple reception portion that are opposite to each other.

14. The suturing method according to claim 13, further comprises an advancing step of advancing the first jaw and the second jaw before the protruding step.

15. The suturing method according to claim 13, further comprises an advancing step of advancing the first jaw and the second jaw before the retracting step.

16. The suturing method according to claim 13, further comprises a step of arranging the advancing first jaw and the second jaw to the most retracted position before the inserting step or a removing step of removing the medical stapler and the endoscope from the inside of the body.

* * * * *